United States Patent [19]
Walker et al.

[11] Patent Number: 6,039,691
[45] Date of Patent: *Mar. 21, 2000

[54] KINETIC ACOUSTIC OCULAR EXAMINATION APPARATUS AND METHOD

[75] Inventors: William F. Walker, Charlottesville, Va.; Cynthia A. Toth; Richard E. Davidsen, both of Durham, N.C.

[73] Assignees: Duke University, Durham, N.C.; Novason Corporation, Charlottesville, Va.

[*] Notice: This patent issued on a continued prosecution application filed under 37 CFR 1.53(d), and is subject to the twenty year patent term provisions of 35 U.S.C. 154(a)(2).

[21] Appl. No.: 09/087,148

[22] Filed: May 29, 1998

Related U.S. Application Data

[60] Provisional application No. 60/048,434, Jun. 2, 1997.

[51] Int. Cl.[7] ............................................. A61B 8/00
[52] U.S. Cl. ............................................ 600/452; 600/443
[58] Field of Search ................................. 600/437, 439, 600/443, 452, 453, 587

[56] References Cited

U.S. PATENT DOCUMENTS

| | | |
|---|---|---|
| 4,771,786 | 9/1988 | Linuma . |
| 4,865,042 | 9/1989 | Umemura et al. ........................ 600/439 |
| 5,088,498 | 2/1992 | Beach et al. ............................. 600/453 |
| 5,459,570 | 10/1995 | Swanson et al. . |
| 5,474,070 | 12/1995 | Ophir et al. ............................. 600/437 |
| 5,487,387 | 1/1996 | Trahey et al. . |
| 5,524,636 | 6/1996 | Saravazyan et al. ..................... 600/587 |
| 5,606,971 | 3/1997 | Sarvazyan . |

OTHER PUBLICATIONS

Tissue Hardness Measurement Using The Radiation Force Ultrasound, Tsuneyoshi Sugimoto, Sadayula Ueha and Kouichi Itoh, Tokyo Institute of Technology, 1990 Ultrasonics Symposium, pp. 1377–1390.

Reports –Ultrasound–Stimulated Vibro–Acoustic Spectrography, Mostafa Fatemi and James F. Greeenlef, Science –Vol. 280, 3 April 1998, pp. 82–85.

Michaels, et al., Retinal Detachment, 1–1138 (The C.V. Mosby Company, St. Louis, 1990).

Byrne, Ultrasound of the Eye and Orbit, 1–505 (Mosby Year Book, St. Louis, 1992).

*Primary Examiner*—Marvin M. Lateef
*Assistant Examiner*—Ali M. Imam
*Attorney, Agent, or Firm*—Nixon & Vanderhye P.C.

[57] ABSTRACT

Soft tissue examination apparatus and method employ an ultrasonic transducer system for generating a series of ultrasound pulses, at least one of which is of sufficiently high intensity to induce physical displacement of the soft tissue. The transducer receives a series of ultrasonic echo pulses and responsively generates a series of data signals indicative of such tissue displacement. A data processor receives the data signals and determines the magnitude of the displacement. In such a manner, the present invention assists in the evaluation and/or diagnosis of biological tissue. Preferably, the apparatus and method of this invention is employed to examine the properties of a subject's vitreous body and thus may be used in the evaluation and/or diagnosis of ocular disorders, such as vitreous traction.

21 Claims, 2 Drawing Sheets

KINETIC ACOUSTIC OCULAR EXAMINATION APPARATUS AND METHOD

DOMESTIC PRIORITY CLAIM

This application is based on, and claims domestic priority rights under 35 USC §119(e) from, U.S. Provisional Patent Application Ser. No. 60/048,434 filed on Jun. 2, 1997, the entire content of which is expressly incorporated hereinto by reference.

GOVERNMENT RIGHTS STATEMENT

This invention was made with Government support under Grant No. 1 R43 EY11456-01 awarded by the National Institutes of Health. The Government has certain rights in the invention.

FIELD OF INVENTION

The present invention relates to acoustic examination of organs. In preferred embodiments, the present invention relates to the use of kinetic acoustic energy for examination of the vitreous body of a mammalian eye so as to assist the attending physician in the early detection and/or diagnosis of ocular disease, degeneration and the like.

BACKGROUND OF THE INVENTION

Each year, a great number of people risk vision loss from conditions involving vitreous traction. Vitreous traction results from changes in the mechanical properties of the vitreous body of the eye. Vitreous traction may act to deform the retina or detach the retina from underlying layers of the eye. If such a condition is left untreated, the retina may degenerate with resulting vision loss. Thus, early and accurate diagnosis of conditions involving the vitreous and retina is essential to determine appropriate treatment to correct or limit progression of the condition and preserve vision.

Unfortunately, many retinal disorders are associated with hemorrhage which prevents visual diagnosis. In these cases diagnosis is currently performed by ultrasonic imaging of the transient vitreal motion resulting from an ocular saccade. (See, Michaels, et al, *Retinal Detachment*, 1-1138 (The C.V. Mosby Company, St. Louis, 1990) and Byrne, *Ultrasound of the Eye and Orbit*, 1-505 (Mosby Year Book, St. Louis, 1992), the entire content of each being expressly incorporated hereinto by reference). Disturbances in vitreal motion indicate points of vitreoretinal adhesion, aiding localization and diagnosis of retinal conditions. However, eye motion makes localization of small targets difficult.

More specifically, in conventional ocular kinetic echography, a standard B-mode imaging system is used to observe motion in the vitreous induced by movement of the eye. The transducer is placed on the eye and the patient is asked to move their eye. This eye movement generates inertial movement of the vitreous. When the eye movement stops, the vitreous continues to move for a short period of time. It is during the eye movement and after movement that the clinician observes the B-mode image for any disturbances in the vitreal motion which may indicate the location of vitreoretinal adhesions which cannot easily be visualized using static ultrasound. During movement and after movement the clinician may also assess the degree of vitreoretinal adhesion at a particular lesion such as a retinal tear. Unfortunately after movement lasts approximately two seconds, so the time available to observe vitreal motion is brief. Also, every eye movement tends to move the region of interest out of the imaging plane and cause probe movement and loss of registration between successive images, making detection and localization of vitreoretinal adhesion extremely difficult.

Recently, a technique has been disclosed in U.S. Pat. No. 5,487,387 to Trahey et al (the entire content of which is expressly incorporated hereinto by reference) whereby solid masses and fluid-filled cysts may be distinguished using an ultrasonic transducer to transmit a plurality of ultrasonic signals into a target lesion within a human body and receive a plurality of reflected signals therefrom. At least one of the plurality of transmitting signals should be of sufficient intensity to initiate movement of any fluid located with the target lesion. A comparison is made of the differences between individual ones of the plurality of reflected signals to detect the presence or absence of fluid movement within the target lesion. Thereafter, a determination may be made as to whether the target lesion is a fluid-filled cyst or a solid mass based upon the presence or absence of fluid within the target lesion.

SUMMARY OF THE INVENTION

Broadly, the present invention is embodied in apparatus and methods whereby ultrasonic energy (e.g., in the form of acoustic pulses) is employed to physically displace relative soft tissue, such as the vitreous body of a mammalian eye. The resulting induced physical displacement may thereafter be used as a means to image the tissue of interest (e.g., using the return echoes from the applied ultrasonic energy and/or by optical coherence tomography techniques) to assist the attending physician in diagnosing ocular disorders. According to the present invention, therefore, localized small targets within an eye or the entire vitreous of the eye can be subjected to physical displacement by the ultrasound energy and imaged simultaneously during such displacements without necessarily involving eye movement by the subject.

These, as well as other, aspects and advantages of the present invention will become more clear after careful consideration is given to the following detailed description of the preferred exemplary embodiments thereof which follow.

BRIEF DESCRIPTION OF THE DRAWING

Reference will hereinafter be made to the accompanying drawing Figures wherein.

DETAILED DESCRIPTION OF THE PREFERRED EXEMPLARY EMBODIMENTS

The outer layer of the eye is the sclera, a tough collagenous layer which protects the eye and helps give it form. Beneath the sclera lie the layers of the choroid, the monolayered retinal pigment epithelium (RPE), the neurosensory retina and then the vitreous body. During embryologic development, the eye cup invaginates and the retina comes to rest against the RPE, with a potential space between these layers. Active fluid pumps in the RPE and interdigitation of the apical microvilli of the RPE with the photoreceptor outer segments of the retina maintain their proximity. The macula (1.5 mm diameter) is a central portion of the retina which is anatomically specialized for high resolution vision. The macula is essential for reading and other tasks which require high resolution.

The vitreous body fills the globe behind the crystalline lens. In youth, the vitreous is a gel consisting of a collagen matrix stiffened by hyaluronic acid molecules. Over time hyaluronic acid diffuses out of the vitreous and eventually its concentration falls low enough that the collagen matrix begins to collapse. As it collapses the formed vitreous moves anteriorly and centrally in the vitreous cavity leaving fluid filled spaces within, posterior and adjacent to it. At the margins of these spaces are collagen fibers which often remain more firmly attached to the retina inducing traction at the points of attachment. Frequent sites of stronger vitreoretinal attachment include the optic nerve, sites over retinal vessels and the vitreous base anteriorly. Less often, the macula may have orthogonal traction attachments through the vitreous or tangential traction attachments through a residual bridging surface of vitreous. Nonetheless, the vitreous body is considered a relatively "soft" tissue (e.g., as compared to other body tissues). As used herein and in the accompanying claims, the term "soft tissue" means tissue having a modulus of elasticity of less than 5.0 N/m$^2$, and typically between about 0.1 N/m$^2$ to about 3.5 N/m$^2$.

Figure 1:
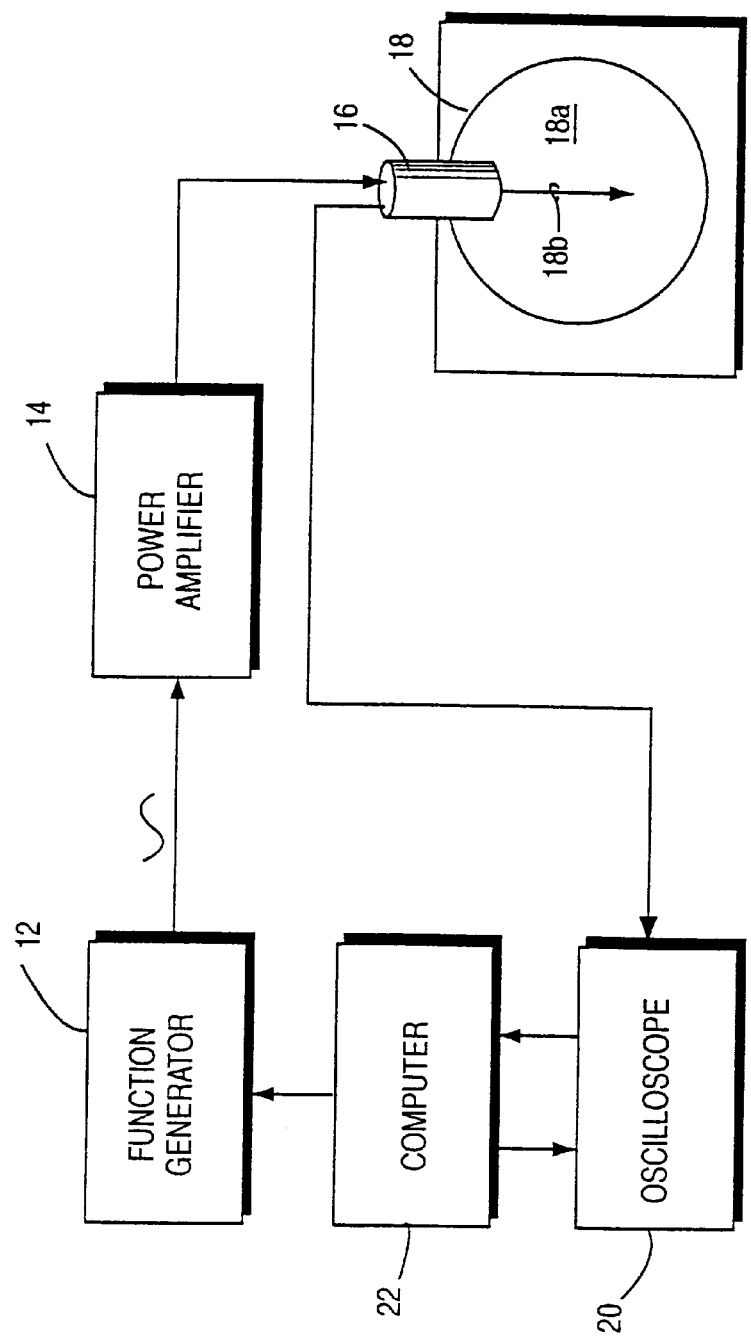
FIG. 1 is a schematic view of a presently preferred ultrasound system that may be employed in the practice of the invention.

The accompanying FIG. 1 depicts schematically one presently preferred embodiment of a clinically realizable ultrasound system 10 in accordance with the present invention. In this regard, the system 10 includes a programmable function generator 12 which generates a series of sinusoidal pulses for transmission. After generation by the function generator 12, the transmit pulses will be amplified by a power amplifier 14. The amplified pulses will then be applied to a piezoelectric transducer 16 which converts the amplified pulses to a series of acoustic pulses. The transducer 16 is placed against the surface of a patient's eye 18. A conventional water path may be inserted between the transducer 16 and the eye 18 if needed. At least one of the pulses, most preferably the leading pulse which is used as a control, is of sufficient intensity and duration to cause motion of the vitreous resulting from acoustic radiation force. That is, at least one of the applied acoustic pulses is of sufficient intensity and duration to cause physical displacement of the vitreal body 18a within the patient's eye 18 as shown schematically by arrow 18b.

Acoustic echoes received by the transducer 16 will be amplified using an amplifier 19 and acquired with a data acquisition system 20. Data will be processed by a computer 22 and displayed by a suitable display system 21. Data may also be stored by the computer 22 for later use. On receiving the echo pulses, isolation from the low output impedance transmit amplifier 14 is provided by a diode circuit between the amplifier 14 and the transducer 16.

The use of algorithms employed in the ultrasonic imaging art, such as cross-correlation, auto-correlation, CW Doppler, sum absolute difference, and the like, may be employed in order to determine tissue displacements. The technique of false peak correction may be used to improve data accuracy. Two dimensional and three dimensional motion tracking methods may also be used to determine displacements. Furthermore, the display of displacement data may be in an image format with displacement magnitude mapped onto the appropriate location in the image. A map of time constant or other viscoelastic properties may also be useful.

Those in this art may find it advantageous to use a different frequency and/or focal distance for imaging than is used to generate the radiation force necessary to cause tissue displacement.

In practice, the ultrasonic transducer that is used to generate an ultrasonic pulse of sufficient magnitude to cause soft tissue displacement during an imaging sequence is most preferably moved from one position relative to the tissue under investigation to another position after each ultrasound cycle. Alternatively, for ultrasound systems utilizing linear or phased array transducers, the effective aperture may be electronically steered or electronically translated between multiple locations. In this way, data may be acquired at each tissue location that can be transformed into two- or three-dimensional images. Furthermore, it may also be desirable that the tissue be "preloaded" prior to data acquisition. That is, the ultrasound transducer may be operated in such a manner that several cycles of the application and relaxation of ultrasound force is applied to the tissue under investigation.

Although reference has been (and will hereinafter be) made to ultrasonic imaging techniques, the present invention may be employed in conjunction with other imaging techniques. For example, physical displacement of the relatively soft tissue can be employed in conjunction with optical imaging techniques, most preferably optical coherence tomography (OCT) as described more fully in U.S. Pat. No. 5,459,570 (the entire content of which is expressly incorporated hereinto by reference). The use of OCT imaging is particularly advantageously employed in those instances where ultrasound imaging may not be satisfactory for the target tissue, such as in the area of the optic nerve and/or macula. Thus, OCT imaging techniques can be employed simultaneously in such areas while the tissue is being displaced by the acoustic force.

As noted above, according to the present invention, at least one relatively high intensity acoustic pulse may precede a series of relatively low intensity acoustic pulses. The relatively high intensity acoustic pulse serves to induce physical displacement of the vitreous body within the patients eye. The echo from the relatively high intensity acoustic pulse also provide a control against which following echo pulses may be compared. The relatively low intensity acoustic pulses, on the other hand, provide measurement signals to allow measurement of the magnitude of the physical displacement of the vitreous body. Alternatively, high intensity pulses may be used both to produce and observe vitreous motion. Most preferably, the present invention will intermittently perturb the vitreous body by providing an intermittent series of relatively high intensity pulses interspersed with a series of relatively low intensity pulses. In such a manner, therefore, the vitreous body will be physically displaced in a discontinuous manner, and the magnitude and/or time course (i.e., the frequency or rate of change) of such discontinuous physical displacement or movement can be sensed by the echoes from the intermediate relatively low intensity pulses. The frequency or time course of application of high intensity pulses may be used to selectively interrogate the low frequency response of tissue. This yields data regarding the viscoelastic properties of the tissue, rather than simply the elastic properties.

EXAMPLES

The present invention will be further illustrated by the following non-limiting Examples.

Example I

External tissue, including muscle and fat, of porcine eyes from freshly slaughtered (within one hour) animals was removed surgically. A 0.1 ml bolus of hyaluronidase solution (500 units) was injected into the eyes so as to break up hyaluronic acid which normally stiffens the vitreous and thereby produce a porcine eye with the mechanical properties more closely mimicking those of middle aged human eyes. The porcine eyes were rotated at room temperature for two hours, following a rest period at room temperature for an additional three hours prior to ultrasonic examination.

Acoustic pulses were applied and echoes acquired using a custom ultrasound system. 8 cycle, 5.0 MHz pulses were transmitted at a repetition rate of 12 kHz. A 5.0 mHz focused piston transducer with a focal radius of 50.8 mm and a diameter of 9.5 mm was used for acoustic transmission and reception. The transducer was excited by eight cycle sinusoidal bursts with a peak amplitudes of roughly sixty volts. The eye was placed at a distance of 35 mm from the transducer to ensure that the focus would lie within the vitreous.

Figure 2:
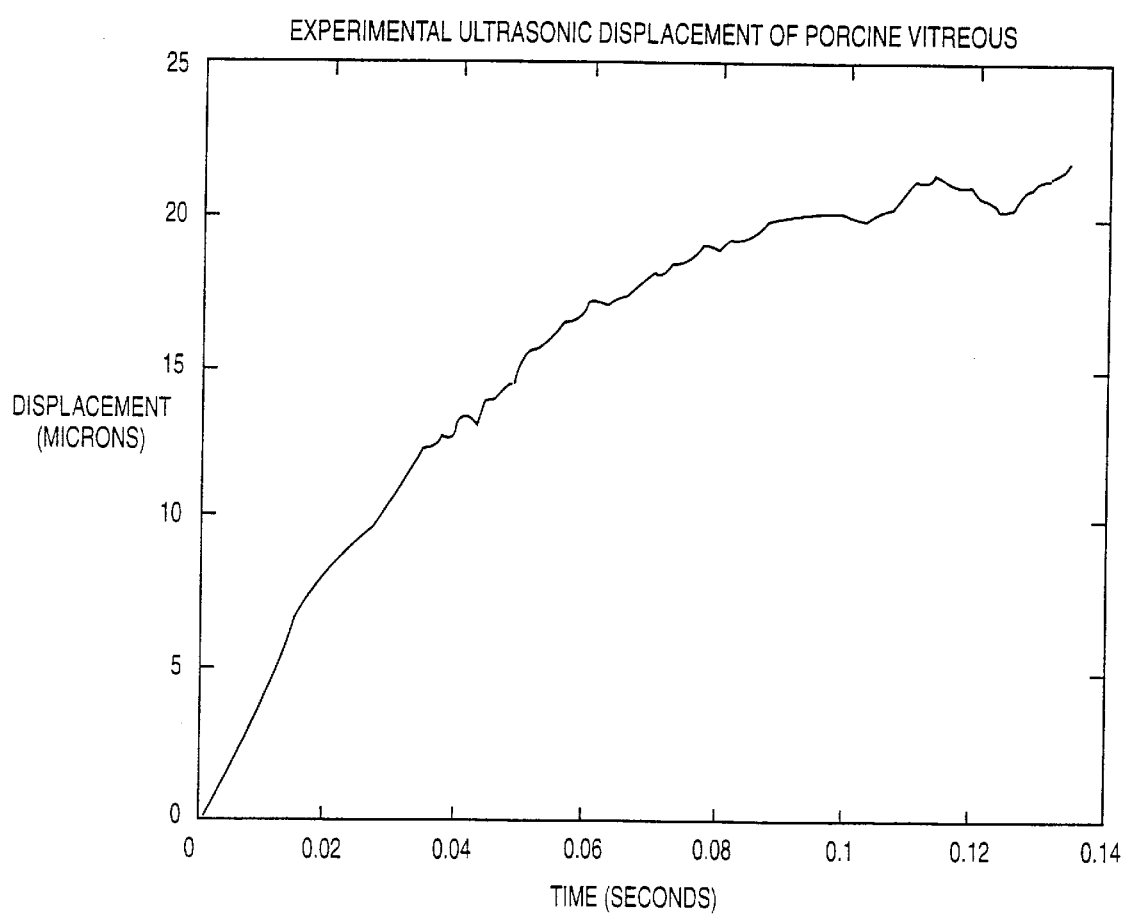
FIG. 2 is data plot of experimental ultrasonic displacement of porcine vitreous (microns) versus time (seconds).

The radio frequency (rf) data acquired from the transducer following the initiation of acoustic transmission showed that the echoes moved away from the transducer when transmission is initiated, but that the motion stops when the radiation force is equal to the resisting force exerted by the vitreous. In addition, the echoes were displayed in a range indicative of origination in the eye. The rf data indicated that acoustic radiation force is adequate to displace vitreous tissue. As shown in accompanying FIG. 2, a data plot of the displacement in microns versus time in seconds indicates that the vitreous displacement followed a decaying exponential curve. The time constant of the curve depicted in FIG. 2 is indicative of the vitreous viscoelasticity. Such a time constant could be readily estimated from the acquired data.

Example II

A phantom was constructed by filling a latex sheath with raw egg white and adding 10 $\mu$m crystal cellulose particles added as ultrasonic scatterers. One element of a split aperture probe, normally designed for Doppler ultrasound techniques, was used to transmit ultrasonic pulses with 15% bandwidth and 8.0 MHz center frequency, at a pulse repetition frequency of 5.0 kHz. The other element of the probe was used to receive returned echoes. The phantom was placed in a water filled tank and the transducer was held by a computer controlled positioning system. The probe was positioned at one side of the phantom and 4000 pulses were transmitted. The echo from every $200^{th}$ pulse was acquired by a digital oscilloscope. Acquired echoes were transmitted to a computer for processing. The transducer was moved laterally roughly 250 $\mu$m and transmission, reception and storage were repeated. This process was repeated until data was acquired throughout most of the phantom.

The second echo acquired from each image was filtered and envelope detected to form a B-Mode image. The image showed the latex membrane clearly visible as a circle, with a hard sponge visible at the bottom of the image. Echoes were visible in the lower portion of the egg white, where scatterers were effectively introduced. However, the upper portion, which lacked scatterers was clearly anechoic.

The delay between echoes acquired from the same image line was estimated using the Sum Absolute Difference Algorithm at a series of ranges. At each image location the total displacement over all pulse firings was stored. An image of tissue stiffness formed using this data was observed to have blue regions indicative that received echo levels were too small to estimate whether motion was present. In this regard, the water surrounding the phantom and the anechoic phantom region both appeared blue. Black regions in the image indicated that the material was not significantly displaced by the application of ultrasound force, and was thus considered stiff. The latex sheath and the sponge both appeared black and thus were considered stiff. The result of the colors in the image, ranging from red to orange to yellow and finally white, indicated decreasing stiffness. Thus, the egg whit contains regions with varying amount of stiffness. However, all are softer than the latex and underlying sponge.

Example III

Example II was repeated except that a modified ennucleated porcine eye was used. The eye was placed under the same conditions as the phantom in Example II, including the use of a latex sheath. The eye was modified through the injection of 1000 IU of collagenase and 5000 IU of Hyaluronidase, to modify its mechanical and ultrasonic properties to better mimic those of aged human vitreous. Images were formed using the same parameters as described above, with the exception that echo data were filtered before processing.

The B-Mode image clearly showed the sclera as a bright circle with the sponge visible beneath the eye. A bright line in the central portion of the eye indicated the border of the lens, with the lens lying in the lower portion of the eye.

A stiffness image of the eye, like that of the phantom of Example II, showed water as a blue color. The lens, sclera and sponge all appeared black because of their relative stiffnesses. The vitreous of the eye showed colors ranging from red to yellow to white, indicating a variety of stiffnesses, all of which were softer than the sponge, sclera and lens. The borders of the vitreous generally appeared darker, possibly because being close to a stiff region made them more resistant to force application.

The present invention has been described above in connection with apparatus and method for examining vitreous displacement and/or time course of the displacement. However, the techniques of this invention may likewise be employed for other relatively soft tissue (e.g., tissue having a modulus of elasticity of less than 5.0 N/m$^2$, and typically between about 0.1 N/m$^2$ to about 3.5 N/m$^2$), for example, cervical mucus.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of examining relatively soft biological tissue comprising the steps of:

(a) generating a series of ultrasound pulses and directing said series of ultrasound pulses into relatively soft biological tissue such that at least one of the pulses is of sufficiently high intensity to induce physical displacement of the tissue; and (b) imaging the physically displaced tissue.

2. The method of claim 1, wherein step (a) is practiced using an ultrasonic transducer.

3. The method of claim 2, wherein step (b) includes sensing returned echoes from said series of ultrasonic pulses, and measuring the magnitude of the physical displacement and/or time course of the tissue using said return ultrasound echoes from said series of pulses.

4. The method of claim 3, wherein steps (a) and (b) are practiced using the same transducer.

5. The method of claim 2, wherein step (a) includes moving said ultrasound transducer from one location to another to acquire data at different locations relative to the tissue, and wherein step (b) includes using said acquired data from said different locations to generate a two or more dimensional image of the tissue.

6. The method of claim 5, wherein said step of moving said ultrasound transducer is practiced by physically moving said transducer from one location to another.

7. The method of claim 5, wherein said step of moving said ultrasound transducer is practiced by electronically steering or translating ultrasound energy between multiple locations.

8. The method of claim 1, wherein step (b) is practiced using optical coherence tomography techniques.

9. The method of claim 1, wherein step (a) is practiced using a continuous series of ultrasonic pulses.

10. The method of claim 1, wherein step (a) is practiced using a varying series of ultrasonic pulses.

11. The method of claim 1, wherein said varying series of ultrasonic pulses is sinusoidal.

12. The method of claim 1, wherein the soft tissue has a modulus of elasticity of less than 5.0 $N/m^2$.

13. The method of claim 10, wherein the soft tissue has a modulus of elasticity of between about 0.1 $N/m^2$ to about 3.5 $N/m^2$.

14. The method of claim 1, wherein said soft tissue is the vitreous body of a mammalian eye.

15. A biological tissue examination apparatus comprising:

an ultrasonic transducer system for generating a series of ultrasound pulses, at least one of said pulses being of sufficiently high intensity to induce physical displacement of relatively soft tissue, and for receiving a series of ultrasonic echo pulses, wherein said transducer responsively generates a series of data signals indicative of said soft tissue displacement;

a data processor for receiving the data signals and determining the magnitude of said soft tissue displacement.

16. The apparatus of claim 15, wherein said transducer system includes an ultrasonic transducer which is selected from the group consisting of piston transducers, phase array transducers, linear array transducers and curved linear array transducers.

17. The apparatus of claim 15, wherein said transducer system includes a transducer, a function generator for generating a predetermined series of ultrasonic pulses, and a power amplifier for receiving said series of ultrasonic pulses from said function generator and applying amplified ultrasonic pulses to said transducer.

18. The apparatus of claim 17, wherein said function generator generates a continuous series of ultrasonic pulses.

19. The apparatus of claim 17, wherein said function generator generates a varying series of ultrasonic pulses.

20. The apparatus of claim 17, wherein said function generator generates a sinusoidal series of ultrasonic pulses.

21. The apparatus of claim 15, wherein said data processor includes a computer.

* * * * *